US011040060B2

(12) United States Patent
Arie Schols et al.

(10) Patent No.: US 11,040,060 B2
(45) Date of Patent: Jun. 22, 2021

(54) FOOD COMPOSITIONS FOR MANAGING BODY WEIGHT

(71) Applicant: DSM IP ASSETS B.V., Heerlen (NL)

(72) Inventors: Hendrik Arie Schols, Wageningen (NL); Paulus De Vos, Groningen (NL); Marco Alexander Van Den Berg, Kaiseraugst (CH); Geert Bruggeman, Drongen (BE); Erik Martinus Adrianus Maria Bruininx, Apeldoorn (NL); Neha Mohan Sahasrabudhe, Groningen (NL); Jan Scholte, Groningen (NL); Lingmin Tian, Wageningen (NL); Anton Johannes Scheurink, Groningen (NL)

(73) Assignee: DSM IP ASSETS B.V., Heerlen (NL)

(*) Notice: Subject to any disclaimer, the term of this patent is extended or adjusted under 35 U.S.C. 154(b) by 0 days.

(21) Appl. No.: 16/700,792

(22) Filed: Dec. 2, 2019

(65) Prior Publication Data

US 2020/0101104 A1   Apr. 2, 2020

Related U.S. Application Data

(62) Division of application No. 15/741,589, filed as application No. PCT/EP2016/066223 on Jul. 8, 2019, now abandoned.

(30) Foreign Application Priority Data

Jul. 10, 2015 (EP) .................................. 15176191

(51) Int. Cl.
| | |
|---|---|
| *A61K 31/732* | (2006.01) |
| *A23L 29/231* | (2016.01) |
| *A23L 33/21* | (2016.01) |
| *A61P 3/04* | (2006.01) |

(52) U.S. Cl.
CPC .......... *A61K 31/732* (2013.01); *A23L 29/231* (2016.08); *A23L 33/21* (2016.08); *A61P 3/04* (2018.01); *A23V 2002/00* (2013.01)

(58) Field of Classification Search
CPC ..... A61K 31/732; A23L 29/231; A23L 33/21; A61P 3/04; A23V 2002/00
USPC ......................................................... 514/54
See application file for complete search history.

(56) References Cited

U.S. PATENT DOCUMENTS

| | | | |
|---|---|---|---|
| 9,149,430 B2 | 10/2015 | Reinhold | |
| 2006/0074052 A1 | 4/2006 | Eliaz | |
| 2006/0141007 A1* | 6/2006 | Beisel | ................. A61K 9/0065 |
| | | | 424/439 |
| 2009/0230799 A1 | 8/2009 | Reinhold | |
| 2010/0247582 A1* | 9/2010 | Sorensen | .............. A23L 29/231 |
| | | | 424/400 |

FOREIGN PATENT DOCUMENTS

| | | |
|---|---|---|
| JP | 2000-189109 | 7/2000 |
| JP | 3165743 | 3/2001 |
| JP | 3165743 | 5/2001 |
| JP | 4504683 | 4/2010 |
| JP | 4509563 | 5/2010 |
| JP | 2011-042604 | 3/2011 |
| WO | WO 03/053169 | 7/2003 |

OTHER PUBLICATIONS

Logan et al. Correlating the structure and in vitro digestion viscosities of different pectin fibers to in vivo human satiety. Food Funct., 2015, 6, 63-71. (Year: 2015).*
He et al. Vicious cycle composed of gut flora and visceral fat: A novel explanation of the initiation and progression of atherosclerosis. Medical Hypotheses (2008) 70, 808-811. (Year: 2008).*
Notice of Reasons for Rejection regarding with JP Appln No. P2017-566097(with English-language translation) dated Jul. 7, 2020.
International Search Report for PCT/EP2016/066223, dated Sep. 9, 2016, 4 pages.
Written Opinion of the ISA for PCT/EP2016/066223, dated Sep. 9, 2016, 6 pages.

* cited by examiner

*Primary Examiner* — Yih-Horng Shiao
(74) *Attorney, Agent, or Firm* — Nixon & Vanderhye P.C.

(57) ABSTRACT

Methods for managing the body mass index, the body fat percentage and/or the distribution of fat storage sites of humans are provided, and more particularly the use of food compositions for managing the body mass index, the body fat percentage and/or the distribution of fat storage sites by administering to a human in need of managing body mass index, body fat percentage and/or distribution of fat storage sites an effective amount of a food formulation comprised of an esterified pectin having a degree of esterification (DE) of less than 65%.

3 Claims, No Drawings

FOOD COMPOSITIONS FOR MANAGING BODY WEIGHT

This application is a divisional of commonly owned U.S. application Ser. No. 15/741,589, filed Jan. 3, 2018 (now abandoned) which is the U.S. national phase of International Application No. PCT/EP2016/066223 filed Jul. 8, 2016, which designated the U.S. and claims priority to EP Patent Application No. 15176191.3 filed Jul. 10, 2015, the entire contents of each of which are hereby incorporated by reference.

This invention relates generally to compositions and methods for managing the body mass index, the body fat percentage and/or the distribution of fat storage sites of humans and particularly to the use of food compositions for managing the body mass index, the body fat percentage and/or the distribution of fat storage sites. The present invention relates to methods, food ingredients and dietary supplements for managing the body mass index, the body fat percentage and/or the distribution of fat storage sites i.e. prevention of a positive energy balance, weight gain and overweight, treatment of overweight and obesity as well as fat reduction for cosmetic purposes. In particular, the food ingredient and dietary supplements of the present invention comprises specific pectin compounds useful for reducing fat storage in the gastrointestinal tract and to induce a negative energy balance and weight loss in subjects who wish to reduce their body weight.

The current way of life in industrialised countries may be characterised by less physical work and increased consumption of fat and carbohydrates, resulting in the energy intake exceeding energy expenditure. This shift in the energy balance causes storage of energy in the body in form of fat, leading to an increase of overweight and obesity, due to the long-term energy imbalance associated with lifestyle.

The percentage of overweight people increases year by year and obesity is a disease that is reaching epidemic proportions in some countries. The health risks associated with overweight and obesity are numerous and it has been shown that these conditions contribute to morbidity and mortality of individuals suffering from diseases such as hypertension, stroke, diabetes mellitus type II, gallbladder disease and ischaemic heart disease. The cosmetic perspective of body fat is also to be considered as the demand for dietary supplements or medicine to gain or maintain a leaner body is constantly increasing.

A common strategy for reducing the risk of overweight and obesity has been to reduce the average energy intake by lowering the dietary fat intake. Dietary fat is a major determinant for energy density of the diet and thereby for energy intake. A reduction in the daily consumption of fat concurrently, with an increase in the consumption of foods rich in complex carbohydrates, is part of the dietary recommendations in many countries.

Surprisingly, it was found that a specific kind of pectin (in regard to its degree of esterification) is useful in decreasing the body mass index, the body fat percentage and/or the distribution of fat storage sites.

By term managing it is meant that the body mass index, the body fat percentage and/or the distribution of fat storage sites is improved or at least stabilized.

The body mass index (BMI), or Quetelet index, is a measure of relative size based on the mass and height of an individual.

The following formula $$\frac{\text{body weight (in kg)}}{(\text{body height (in m)})^2} = BMI$$

is representing the BMI

The index was devised by Adolphe Quetelet between 1830 and 1850. The BMI for a person is defined as their body mass divided by the square of their height—with the value universally being given in units of $kg/m^2$. So if the weight is in kilograms and the height in metres, the result is immediate, if pounds and inches are used, a conversion factor of 703 $(kg/m^2)/(lb/in^2)$ must be applied.

| Category | BMI range - $kg/m^2$ |
|---|---|
| Very severely underweight | less than 15 |
| Severely underweight | from 15.0 to 16.0 |
| Underweight | from 16.0 to 18.5 |
| Normal (healthy weight) | from 18.5 to 25 |
| Overweight | from 25 to 30 |
| Obese Class I (Moderately obese) | from 30 to 35 |
| Obese Class II (Severely obese) | from 35 to 40 |
| Obese Class III (Very severely obese) | over 40 |

The body fat percentage of a human or other living being is the total mass of fat divided by total body mass; body fat includes essential body fat and storage body fat. Essential body fat is necessary to maintain life and reproductive functions. The percentage of essential body fat for women is greater than that for men, due to the demands of childbearing and other hormonal functions. The percentage of essential fat is 3-5% in men, and 8-12% in women.

Storage body fat consists of fat accumulation in adipose tissue, part of which protects internal organs in the chest and abdomen. The minimum recommended total body fat percentage exceeds the essential fat percentage value reported above. A number of methods are available for determining body fat percentage, such as measurement with calipers or through the use of bioelectrical impedance analysis.

While BMI largely increases as adiposity increases, due to differences in body composition, other indicators of body fat give more accurate results; for example, individuals with greater muscle mass or larger bones will also have higher BMIs.

Two main types of fat can be distinguished: visceral fat and subcutaneous fat. Subcutaneous fat is stored under the skin. Visceral fat is body fat that is stored within the abdominal cavity and is therefore stored around a number of important internal organs such as the liver, pancreas and intestines. Visceral fat or abdominal fat (also known as organ fat or intra-abdominal fat) is located inside the abdominal cavity, packed between the organs (stomach, liver, intestines, kidneys, etc.). Visceral fat is different from subcutaneous fat underneath the skin, and intramuscular fat interspersed in skeletal muscles. Fat in the lower body, as in thighs and buttocks, is subcutaneous and is not consistently spaced tissue, whereas fat in the abdomen is mostly visceral and semi-fluid. Visceral fat is composed of several adipose depots, including mesenteric, epididymal white adipose tissue (EWAT), and perirenal depots. Visceral fat is considered adipose tissue whereas subcutaneous fat is not considered as such.

Visceral fat can be classified in various subclasses, including but not limited to: pericardial fat, perirenal fat, periadrenal fat, retroperitoneal fat, mesenteric fat, omental fat, epididymal fat. The visceral fat around the intestines is sometimes referred to as intestinal fat.

Visceral fat is sometimes referred to as 'active fat' because research has shown that this type of fat plays a distinctive and potentially dangerous role affecting how our hormones function. Storing higher amounts of visceral fat is associated with increased risks of a number of health problems including type 2 diabetes. Carrying a high amount of visceral fat is known to be associated with insulin resistance, which can lead to glucose intolerance and type 2 diabetes.

Fibres (also pectin fibers) are known to be used to achieve a satiety effect when consumed. It was found that the use of specific pectins has even more positive and surprising effects.

Now the embodiment of the present invention is useful to decrease the BMI, to decrease the body fat percentage and/or the to shift the distribution of fat storage sites of humans.

The term "manage" is used to define these effect.

Therefore the present invention relates to a composition comprising at least one pectin with an degree of esterification less than 65% for managing the body mass index, the body fat percentage and/or the distribution of fat storage sites of humans.

In a preferred embodiment the present invention relates to a composition comprising at least one pectin with an degree of esterification less than 65% for managing the levels and/or percentage of visceral fat of humans.

In another preferred embodiment the present invention relates to a composition comprising at least one pectin with an degree of esterification less than 65% for managing the levels and/or percentage of mesenteric or gut fat of humans.

Pectin is a structural heteropolysaccharide contained in the primary cell walls of terrestrial plants. It is produced commercially as a white to light brown powder, mainly extracted from citrus fruits, and is used in food as a gelling agent, particularly in jams and jellies. It is also used in fillings, medicines, sweets, as a stabilizer in fruit juices and milk drinks, and as a source of dietary fiber. Pears, apples, guavas, quince, plums, gooseberries, oranges, and other citrus fruits contain large amounts of pectin, while soft fruits like cherries, grapes, and strawberries contain small amounts of pectin. But also other plant sources than fruits can comprise pectin. For example, pectin can be sourced from potato, soy, sugar beet, chicory, carrot, tomato, pea, parsnip, and (green) beans. All these lists are not exhaustive at all. Only the main sources are listed.

The following illustration shows parts of the structure of pectin as well as (partially) esterified pectin.

Structure of Pectin (Polygalacturonic Acid)

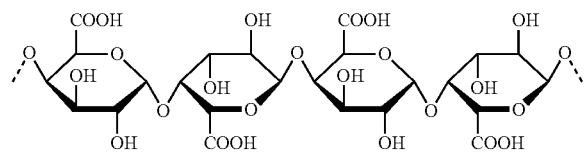

Structure of (Partially) Methylated Pectin

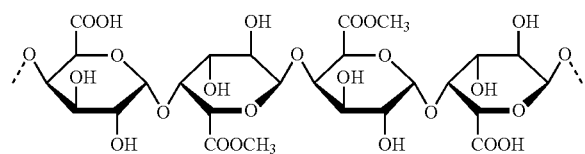

In the above shown formula the esterification is a methylation, but also other groups can be used (such as acetyl). Pectin can be esterified with one group (such as $CH_3$ or $COCH_3$) or with more than one group in the same oligomer structure. Acetylation usually occurs at the oxygen in the hydroxyl group on position 2 and/or 3, while methylation usually occurs at the carboxyl group on position 5.

In the scope of the present invention the degree of esterification is used to describe the percentage of esterified pectin monomer units in the backbone.

Pectin is a complex polysaccharide composed of a α-1, 4-linked D-galacturonic acid (GalA) backbone (the so-called homogalacturonan or smooth region) and segments consisting of alternating sequences of α-(1,2)-linked L-rhamnosyl and α-1,4-linked D-galacturonosyl residues ramified with side chains of arabinans, arabinogalactans and galactans (branched rhamnogalacturonans or hairy regions). Pectins are decorated with neutral sugars (NS), mainly being galactose and arabinose attached to the rhamnose moiety in the backbone.

Commercial pectins usually contain low amounts of neutral sugar as a result of the acid extraction (the neutral sugar content is around 5%). Other structural elements of pectins are xylogalacturonan and rhamnogalacturonan II. Rhamnogalacturonan II is carrying peculiar sugar residues such as Api (D-apiose), AceA (3-C-carboxy-5-deoxy-L-xylose), Dha (2-keto-3-deoxy-D-lyxo-heptulosaric acid) and Kdo (2-keto-3-deoxy-D-manno-octulosonic acid). The relative proportions of these different structural elements may vary significantly for different plant origins and the various derived commercial products.

The various structural elements of pectin can be esterified. The major types of esterification are: O-methyl, O-acetyl and O-feruloyl. Not excluding any other types of esterification. Most of the esterifications reside in the homogalacturonan region on the GalA residues. The GalA residues can be thus present with free carboxyl groups or esterified at one or more of the carboxyl groups. Esterification can occur as mono-esterification, but also as double esterification of single GalA residues. Not excluding any other numbers of esterification. The esterification on a single residue can be through a single type of alkyl group (i.e. methyl) or a single type of acyl group (i.e. acetyl). Not excluding any mixed type esterification. Thus, GalA can be methylated (leading to 0 or 1 methyl groups per GalA residue) or can be acetylated (leading to 0, 1 or 2 acetyl groups respectively on the oxygen of the hydroxyl group on the C-2 and/or C-3). The latter occurs as such in sugar beet and potato pectins.

The pectins of the current invention typically have a MW size distribution of 5 and 800 kDa. Preferably the MW size distribution is between 5 and 400 kDa. Preferably, the majority of the pectin molecules in a given pectin composition has a MW below 200 kDa. Preferably, the majority of the pectin molecules in a given pectin composition has a MW below 100 kDa.

The degree of esterification (DE) is by definition the amount of esters (in moles) present per 100 moles of total galacturonic acids (free GalA and substituted GalA summed together). As most commercial pectins are essentially having esterifications of the methyl-ester type, the DE is often expressed as the degree of methylation (i.e. DM). In that case, the degree of esterification is by definition the amount of methyl-esters (in moles) present per 100 moles of total galacturonic acids (free GalA and substituted GalA summed together). In the case that the esterification is of the acetyl type, the DE is often expressed as the degree of acetylation (i.e. DA). In that case, the degree of esterification is by definition the amount of acetyl-esters (in moles) present per 100 moles of total galacturonic acids (free GalA and substituted GalA summed together). In the case of multiple types of esterification in a single pectin sample, the DE is often expressed splitted in to a degree of methylation (i.e. DM) and a degree of acetylation (i.e. DA). These are calculated as described above. Alternatively, the DE can be expressed as the degree of esterification, defined the by amount of galacturonic acid residues modified with one or more esterifications—either being of the methyl or the acetyl type—(in moles) present per 100 moles of total galacturonic acids (free GalA and substituted GalA summed together).

In the context of this invention the term degree of esterification (DE) is used, and the percentages described are always based on the amount of GalA residues which are substituted through esterification (i.e. methylation). A DE of 50 means that 50% of all possible GalA residues are esterified (i.e. methylated).

The following patent application is related to the use of esterified pectins, more specifically it is related to the use of esterified pectins with a specific degree of esterification.

The following distinction is made among the esterified pectins:
(i) Low-esterified pectins
(ii) High-esterified pectins.

Low-esterified pectins have a degree of esterification (DE) of less than 50%. This means that less than 50% of the possible positions are esterified.

High-esterified pectins have a DE of more than 50%. This means that more than 50% of the possible positions are esterified.

DE values for commercial HM-pectins typically range from 60 to 75% and those for LM-pectins range from 20 to 40% (Sriamornsak, 2003, Silpakorn University International Journal 3 (1-2), 206-228).

As mentioned above pectins are present in almost all higher plants. Several by-products of the food industries are used for their extraction, such as citrus peels (by-product of citrus juice production), apple pommace (by-product of apple juice manufacture), sugar beet (by-product of the beet-sugar industry) and in a minor extend potatoes fibres, sunflower heads (by-product of oil production) and onions (May, 1990, Carbohydr. Polymers, 12: 79-99). A typical process to extract HM pectins from the pomace or peels is in hot diluted mineral acid at pH1-3 at 50-90° C. during 3-12 hours (Rolin, 2002, In: Pectins and their Manipulation; Seymour G. B., Knox J. P., Blackwell Publishing Ltd, 222-239). Dry citrus peels contain 20 to 30% of pectin on a dry matter basis, lower amounts are present in dried apple pomace (10 to 15%) (Christensen, 1986, Pectins. Food Hydrocolloids, 3, 205-230). By adding alcohol (usually isopropanol but methanol or ethanol are also used) the pectins are precipitated. Finally, the gelatinous mass is pressed, washed, dried and ground (May, 1990, Carbohydr. Polymers, 12: 79-99). Depending on the process conditions, pectins with a DM from 55 to 80% are obtained (Rolin, 2002, In: Pectins and their Manipulation; Seymour G. B., Knox J. P., Blackwell Publishing Ltd, 222-239).

Low-methylated (LM) pectins can be obtained by de-esterification of high-methylated (HM) pectins mainly by controlling the acidity, the temperature and the time during extraction. To produce other types of pectins, esters can be hydrolysed by the action of acid or alkali either before or during an extraction, as concentrated liquid or in the alcoholic slurry before separation and drying. When alkali is used, the reaction has to be performed at a low temperature and in aqueous solutions to avoid β-eliminative degradation of the polymers (Kravtchenko et al, 1992, Carbohydrate Polymers, 19, 115-124). LM pectins can also be extracted with aqueous chelating agents such as hexametaphosphate (e.g. potato pectins) (Voragen et al., 1995, In: Food polysaccharides and their applications; Stephen A. M., New York: Marcel Dekker Inc, 287-339). The use of the enzyme pectin methyl-esterase (PME) for the production of LM pectins can be an alternative for the chemical extraction (Christensen, 1986, Pectins. Food Hydrocolloids, 3, 205-230). The conditions and time of the different reactions are varied leading to pectins with a different DE, even as low as a DE of zero.

Although, commercial LM pectins are almost exclusively derived from HM pectins, there are natural sources of LM pectin, such as mature sunflower heads (Thakur et al, 1997, Critical Reviews in Food Science and Nutrition, 37(1):47-73).

The DE can be determined by commonly known methods.

For example, the degree of esterification can be determined using several methods such as titration (Food Chemical Codex, 1981), IR spectrometry (Gnanasambandam & Proctor, 2000, Food Chemistry, 68, 327-332; Haas & Jager, 1986, Journal of Food Science, 51(4), 1087-1088; Reintjes et al, 1962, Journal of food sciences, 27, 441-445) and NMR spectrometry (Grasdalen et al, 1988, Carbohydrate Research, 184, 183-191). Other methods using HPLC (Chatjigakis et al., 1998, Carbohydrate Polymers, 37, 395-408; Levigne et al., 2002, Food Hydrocolloids, 16(6), 547-550; Voragen et al, 1986, Food Hydrocolloids, 1(1), 65-70) and GC-headspace (Huisman et al, 2004, Food Hydrocolloids, 18(4), 665-668; Walter et al, 1983, Journal of Food Science, 48(3), 1006-1007) analysing the methanol content after saponification of the pectins have been developed. A capillary electrophoresis (CE) method has been developed to determine the DM of the polymers as such (Jiang et al, 2005, Food Chemistry, 91, 551-555; Jiang et al, 2001, of Agricultural and Food Chemistry, 49, 5584-5588; Zhong et al, 1998, Carbohydrate Research, 308, 1-8; Zhong et al, 1997, Carbohydrate Polymers, 32(1), 27-32). An advantage of the CE method is that the GalA content of the samples is not required to calculate the DM whereas the GalA values have to be known prior to the DM calculation following GC headspace and HPLC methods.

Surprisingly if was found that the use of pectins with a DE of less than 65% is advantageous for managing the body mass index, the body fat percentage and/or the distribution of fat storage sites. The pectins according to the present invention are preferably not amidated (has no amide functions).

Therefore the present invention also relates to an esterified pectin or a mixture of esterified pectins for the use in % in managing the body mass index, the body fat percentage and/or the distribution of fat storage sites of humans, wherein the pectin has a DE of less than 60%.

The degree of esterification in the context of the present invention is preferably determined by the HPLC method as described by A. G. J. Voragen, H. A. Schols and W. Pilnik, in the publication titled "Determination of the degree of methylation and acetylation of pectins by h.p.l.c,", published in Food Hydrocolloids, volume 1, issue 1, pages 65-70, 1986.

Furthermore the present invention relates to a method (M) of managing the body mass index, the body fat percentage and/or the distribution of fat storage sites of humans by administering to humans esterified pectins (or a mixture of esterified pectins), wherein the pectins have a degree of esterification of less than 65%.

In the context of the present the pectins can be obtained from any known sources. A list of suitable sources is given above. By using one of the processes as described above, the pectins with the correct DE are obtained.

Preferably the DE of the pectin is less than 60%, more preferably less than 55%, especially preferred less than 50%.

Therefore the present invention also relates to an esterified pectin or a mixture of esterified pectins for the use in % in managing the body mass index, the body fat percentage and/or the distribution of fat storage sites of humans, wherein the pectin has a DE of less than 60%.

Therefore the present invention also relates to an esterified pectin or a mixture of esterified pectins for the use in % in managing the body mass index, the body fat percentage and/or the distribution of fat storage sites of humans, wherein the pectin has a DE of less than 55%.

Therefore the present invention also relates to an esterified pectin or a mixture of esterified pectins for the use in % in managing the body mass index, the body fat percentage and/or the distribution of fat storage sites of humans, wherein the pectin has a DE of less than 50%.

Therefore the present invention also relates to a method ($M_1$), which is method (M), wherein the pectin has a DE of less than 60%.

Therefore the present invention also relates to a method ($M_1'$), which is method (M), wherein the pectin has a DE of less than 55%.

Therefore the present invention also relates to a method ($M_1''$), which is method (M), wherein the pectin has a DE of less than 50%.

Usually the pectin has a DE of at least 1%, preferably of at least 2, more preferably of at least 3%. Therefore there is a range of 1-65%, 2-65%, 3-65%, 1-60%, 2-60%, 3-60%, 1-55%, 2-55% and 3-55%.

Commercial pectins can be a mixture of several populations: the distribution of the substituents can differ in an intramolecular level (within one single pectin polymeric chain) or in an intermolecular level (within one single pectin sample). This holds for all substituents, thus the sugars as well as the esterifications, and therefore both categories are meant with the word 'substituents' in the following. The substituents can be distributed completely at random. This random distribution can follow an even distribution pattern, when the substituents are regularly distributed over a single pectin polymeric chain, leading to a more homogenous pectin polymeric chain. If all pectin polymeric chains in a single pectin sample are of the same homogenous type, also the sample can be called homogeneous.

However, a single homogeneous pectin polymeric chain can be present in a composition with other homogenous pectin polymeric chains but having a different intramolecular (but still homogeneous) distribution of the substituents. In this case, the pectin sample should be considered heterogeneous. Furthermore it is also possible to modify the esterified pectin according to the present invention. One of the possible modifications is amidation. Amidated pectin is a modified form of pectin. In that case some of the galacturonic acid is converted with ammonia to carboxylic acid amide. This is done according to well-known processes. The presence of an amide group is typically at the C-6 position of the amidated GalA residues. If pectin is amidated, the DE is often expressed as the degree of amidation (i.e. DAM). In that case, the degree of esterification is by definition the amount of amides (in moles) present per 100 moles of total galacturonic acids (free GalA and substituted GalA summed together).

Other possible modifications of pectins are ethyl or propyl.

Preferably the esterification type of the pectin is either methylation and/or acetylation, more preferably methylation.

Therefore the present invention also relates to an esterified pectin or a mixture of esterified pectins for the use in % in managing the body mass index, the body fat percentage and/or the distribution of fat storage sites of humans, wherein the esterification type of the pectin is either methylation and/or acetylation Therefore the present invention also relates to an esterified pectin or a mixture of esterified pectins for the use in % in managing the body mass index, the body fat percentage and/or the distribution of fat storage sites of humans, wherein the esterification type of the pectin is methylation.

Therefore the present invention also relates to a method ($M_1$), which is method (M), wherein the esterification type of the pectin is either methylation and/or acetylation.

Therefore the present invention also relates to a method ($M_1'$), which is method (M), wherein the esterification type of the pectin is methylation.

Methods to characterize the different components (i.e. GalA content, neutral sugar content, degree of methylesterification, degree of actetylation, degree of amidation, distribution of the non-methyl-esterified GalA, molecular weight) of natural, modified as well as commercial pectins are well described in the PhD thesis of Stéphanie Guillotin (Studies on the intra- and intermolecular distributions of substituents in commercial pectins. Wageningen University, The Netherlands, 2005. ISBN 90-8504-265-8).

As described above the specific pectins are used for managing the body mass index, the body fat percentage and/or the distribution of fat storage sites.

Surprisingly, it was found that pectins with a low degree of esterification (i.e. low DE) enable a reduction is the percentage of visceral fat.

The amount of pectin, which is used can vary (depending on the person). It depends on the body weight. Usually an amount between 0.01 and 5 g pectin with a DE of less than 65% per Kg body weight and per day is desired.

The pectin, which is ingested can be in any form. It is possible to use the pectin as such or in a mixture with other ingredients.

The ingredients which are used are usually chosen in regard to the use of the mixture. The ingredient can serve to improve the properties of the mixture or when the mixture is used to be formulated into a final composition to improve the final composition.

The ingredients can serve of one or more purpose. It is clear that such ingredients must be food grade (depending on its use).

The pectin can also be part of a food product, whereas the food product can be in any commonly known and used form.

The amount of pectin a specific food product depends on the kind of food product. It is also dependent on the usual amount a person consumes. The more a person consumes the lower the amount can be in the food product to reach the desired amount of pectin.

The following examples serve to illustrate the invention.

EXAMPLES

Example 1 Incorporation of LM Pectin in Diets Leads to More and Smaller Meals Rat Feeding Trial Set-Up 17 Male Wistar rats (weight±320 g; Harlan Netherlands BV, Horst, The Netherlands) were individually housed in TSE cages in a climate-controlled room (21 C±1) under a 12 h:12 h light-dark cycle (lights on at 10:00 AM). These specialized cages were equipped with food weighing sensor for continuous registration of food intake for multiple days (TSE Systems GmbH, Bad Homburg, Germany) to monitor circadian feeding patterns, meal sizes and meal numbers. Circadian food intake patterns were calculated as an average of the last two consecutive days, the first day was used for adaptation. These plexiglass cages (40×23×15 cm) consist of a sensitive weight balanced food station (stainless steel food container for standard size food pellets). Animals were maintained ad libitum on the diets. Water was available ad libitum throughout the study. Food intake and body weights were measured daily at 10 AM. For weighing a laboratory scale was used (sensitivity 0.1 gram). Experiments were approved by the Ethical Committee of Animal Experiments of the University of Groningen.

All animals were instrumented with chronic heart catheters bilaterally in the jugular vein allowing stress free blood sampling during an intravenous glucose tolerance test (IVGTT). Surgeries were carried out under general isoflurane (2%) anesthesia. Animals had at least 10 days to recover before the start of the experiments. Cannulas were checked every week for patency.

The full trial lasted 11 weeks:
- week1: meal pattern measurements (TSE)
- week3: Blood sampling during a single meal of 1.5 grams
- week4: meal pattern measurements (TSE)
- week6: Intravenous Glucose Tolerance Test
- week9: meal pattern measurements (TSE)
- week11: carcass analysis Diets 9 rats were fed with a control diet, while 8 rats were fed with pectin enriched diet.

The composition of the diets was as follows: 95% chow RMH-B meal (obtained from Arie Blok, Woerden, the Netherlands) and 5% Pectin (see Pectin sources). The diets were prepared by mixing all components (including 0.25% TiO2 as marker) with water to 600 ml/kilo in an industrial mixer until a homogeneous mixture/dough was obtained. After 20 minutes of mixing, the diets were pelleted using a pelleting machine (diameter 1.0 cm). The obtained pellets were dried for 48 hours using compressed air at room temperature.

Pectin Sources

Pectin with a DE 33 were isolated from citrus and obtained from Herbstreith & Fox (Neuenburg/Württingen, Germany).

Feeding Pattern Analyses

During the second meal pattern measurements the animals were observed and measurements were performed for 48 hours. The obtained data was averaged over all animals fed on a certain diet and is presented in the table below. Statistical analyses were performed using student T test.

|  | Control diet | Pectin DE 33 diet |
|---|---|---|
| Number of meals | 20.56 ± 0.84 | 23.25 ± 0.82 |
| Average meal size (g) | 1.99 ± 0.07 | 1.75 ± 0.11 |
| Average meal duration (min) | 8.22 ± 0.54 | 9.22 ± 0.25 |
| Average eating speed (g/min) | 0.32 ± 0.04 | 0.21 ± 0.01 |

Surprisingly, pectin fed animals consumed significantly more meals which are smaller in size. Still, the total amount eaten in the period for both diets is not significantly different (40.92 vs 40.69 grams), meaning that the reduced meal size is due to a satiating effect.

Example 2 Incorporation of LM Pectin in Diets Leads to Improved Homeostasis of Blood Glucose Levels The rat trial was as described in example 1.

Intravenous Glucose Tolerance Test

To assess the effects of pectin addition to the diet on glucose regulation, rats were subjected to an intravenous glucose tolerance test (IVGTT). The IVGTT was performed during week6. The IVGTT was performed during the third and fourth hour of the light phase. Food was removed at lights on and rats were connected to the blood sampling and infusion tubes at least one hour before the IVGTT. During the IVGTT, a 15% glucose solution was infused for 30 minutes at a rate of 0.1 ml/min. The start of the infusion was designated time point=0 min. Blood samples (0.2 ml) for determination of blood glucose levels were taken before, during, and after the infusion of glucose at time points=−10, −1, 5, 10, 15, 20, 25, 30, 35, 40, and 50 minutes. Note that the glucose infusion prevented any hypovolemic effect of the blood sampling. Blood samples were collected in EDTA (20 microliter/ml blood) containing tubes on ice. Blood was centrifuged at 2600 g for 10 minutes and plasma was stored at −20 C until analysis. Blood glucose levels were measured by Hoffman's ferrocyanide method (Hoffman, W. S. (1937). J. Biol Chem, 120, 51).

Results

Surprisingly, the data demonstrated that blood glucose levels after the 30-minutes intravenous infusion of glucose are lower (indicated by the grey boxes) in rats fed on the diet containing pectin with a DE of 33 as compared to the blood glucose levels of the rats fed on the control diet. Meaning that mammals fed on diets containing low DE pectin are better equipped to controlling their blood sugar levels, by levelling of peak concentrations, which is beneficial for preventing developing obesity, as well as managing the body mass index and/or the body fat percentage.

| Diet | | Time points (min) | | | | | | | | | | |
|---|---|---|---|---|---|---|---|---|---|---|---|---|
| | | −11 | −1 | 5 | 10 | 15 | 20 | 25 | 30 | 35 | 40 | 50 |
| Control | Glucose (mmol) | 5.56 | 5.71 | 7.37 | 8.55 | 9.49 | 10.05 | 10.34 | 10.61 | 8.73 | 7.16 | 5.86 |
| | SEM | 0.21 | 0.18 | 0.23 | 0.19 | 0.28 | 0.28 | 0.30 | 0.25 | 0.18 | 0.18 | 0.17 |

-continued

| | | Time points (min) | | | | | | | | | | |
|---|---|---|---|---|---|---|---|---|---|---|---|---|
| Diet | | −11 | −1 | 5 | 10 | 15 | 20 | 25 | 30 | 35 | 40 | 50 |
| Pectin DE 33 | Glucose (mmol) | 5.65 | 5.62 | 7.55 | 8.68 | 9.50 | 9.36 | 9.52 | 9.60 | 7.83 | 6.49 | 5.72 |
| | SEM | 0.11 | 0.12 | 0.23 | 0.28 | 0.51 | 0.32 | 0.35 | 0.32 | 0.24 | 0.33 | 0.27 |

Example 3 Incorporation of LM Pectin in Diets Leads to Improved Homeostasis of Plasma Insulin Levels The rat trial was as described in example 1.
Blood Sampling During a Single Meal of 1.5 Grams The rats were fasted for 7 h (induce hungry animals), after which they were provided with 1.5 g of their diet. Blood samples (0.2 ml) for determination of plasma insulin levels were taken through the cannula at time points=−5, 0, 1, 2.5, 5, 7.5, 10, 15 and 20 minutes. Blood samples were collected in EDTA (20 microliter/ml blood) containing tubes on ice. Blood was centrifuged at 2600 g for 10 minutes and plasma was stored at −20 C until analysis. Plasma levels of insulin were measured by Millipore Rat Insulin Radioimmunoassay (Linco Research, St Charles, Mo., USA).

Results

Surprisingly, the data demonstrated that plasma levels of insulin after feeding were lower (indicated by the grey boxes) in rats fed on the diet containing pectin with a DE of 33 as compared to the plasma levels of insulin of the rats fed on the control diet. Meaning that mammals fed on diets containing low DE pectin are better equipped to controlling their plasma levels of insulin, thereby lowering the chances of so-called hyperinsulinemia, which is a risk factor for developing type 2 diabetes, and thereby acts positively towards managing the body mass index, the body fat percentage and/or the distribution of fat storage sites.

| | Control diet | | Pectin DE 33 diet | |
|---|---|---|---|---|
| | Grams (or g/g for the ratio) | Relative vs body weight (%) | Grams (or g/g for the ratio) | Relative vs body weight (%) |
| Total fat | 76.03 ± 3.26 | 19.5 | 67.74 ± 2.51 | 17.8 |
| Visceral fat | 21.66 ± 1.22 | 5.5 | 17.86 ± 1.21 | 4.7 |
| Gut fat | 4.46 ± 0.23 | 1.1 | 3.51 ± 0.31 | 0.9 |
| Ratio fat:lean mass | 0.54 ± 0.03 | n.a | 0.45 ± 0.03 | n.a. |

Surprisingly, pectin fed animals have a reduced absolute as well as relative percentage of fat. This is also visible for the amount and relative percentage of visceral and gut fat.

Example 5 Incorporation of LM Pectin in Diets Leads to More and Smaller Meals

Piglet Feeding Trial Set-Up

Piglets were housed in weaner facilities pens with 7 (2.56×1.26 m) or 9 piglets per pen (1.3×2.85 m). These pens have been built according to practical regulations, resulting in respectively 0.44 and 0.40 m2 per piglet. A total of 27 pens (replicates) per treatment were used. Per treatment 4 of these replicates were housed in pens equipped with IVOG® feeding stations (Individual Feed Intake Recording in group housing; Isentec, Marknesse, The Netherlands) for weaning pigs. These pens contained 8 piglets per pen (1.75×3.00 m)

| | | Time points (min) | | | | | | | | |
|---|---|---|---|---|---|---|---|---|---|---|
| Diet | | −5 | 0 | 1 | 2.5 | 5 | 7.5 | 10 | 15 | 20 |
| Control | Insulin (ng/ml) | 0.96 | 1.36 | 1.98 | 3.17 | 3.85 | 4.80 | 4.91 | 4.07 | 3.28 |
| | SEM | 0.08 | 0.10 | 0.37 | 0.43 | 0.41 | 0.38 | 0.34 | 0.39 | 0.49 |
| Pectin DE 33 | Insulin (ng/ml) | 0.91 | 1.02 | 1.29 | 2.58 | 2.74 | 4.45 | 4.27 | 4.25 | 3.00 |
| | SEM | 0.08 | 0.09 | 0.27 | 0.32 | 0.29 | 0.67 | 0.52 | 0.48 | 0.46 |

Example 4 Incorporation of LM Pectin in Diets Leads to Reduced Fat Deposition

The rat trial was as described in example 1. After sacrifice a carcass analysis was performed to determine the amount of fat. Liver, stomach, gut (ilium to rectum), spleen, kidneys were removed and weighed. Retroperitoneal and epidydimis fat was weighed as well. The fat content from the skin, carcass and gut was determined using a petroleum based Soxlet fat extractor. Visceral fat here was defined as the total of intestinal fat, epidydimal fat and retroperitoneal fat.

resulting in 0.65 m2 per piglet. The housing conditions were typical for Dutch pig husbandry, operated according to the Dutch IKB farm standards. Each pen was equipped with a dry feeder and piglets were given ad libitum access to feed and water during the whole post-weaning period. The floor in the pens within a unit was a fully slatted, plastic floor. Enrichment (chain with a play ball) was provided as well. Environmental conditions during the trial (temperature and ventilation rate) were automatically controlled, and were adjusted to the age of the pigs. The start temperature in the weaner pens was 30 C and gradually decreased to 24 C over 35 days. The pigs had the following characteristics:

Animals: 828 weaned piglets
Origin animals: Laverdonk swine herd
Breed: Pietrain×Topigs20

Gender: Males and females
Age at start: On average 26 days (at weaning)
Age at end: On average 61 days
Body weight at start: On average 7.4 kg (at weaning)
Body weight at end: On average 18.2 kg
Dietary Treatments and Feeding Four experimental treatments (=diets) were tested. The treatments were:

| Diet | Description | Code |
|---|---|---|
| 1 | Control | 7% untreated SBM |
| 2 | Pectin soybean meal | 7% processed SBM |
| 3 | Pectin DE33 | 3% pectin 33% DM |
| 4 | Pectin DE33 | 3% pectin 55% DM |

Treatment 1 was the control and contained 7% soybean meal (SBM) as a reference. In treatment 2, the SBM was pre-treated by autoclaving and 7% of the resulting modified SBM was included in the diets (exchanged for untreated SBM). Treatment 3 and 4, were similar to the control but here 3% lemon pectins were replacing 3% SBM. The experimental diets were produced by Research Diet Services (The Netherlands). Piglets had ad libitum access to feed and water.
Number of treatments: 4
Number of replicate pens: 27 per treatment
Number of batches: 6
Period 1: Weaner period, D0-D9
Period 2: Nursery period, D9-D35
Day 0: Day of weaning (Wednesday)
Diets
Feed Compositions (in g/kg):

| | Weaner diet | | | | Piglet diet | | | |
|---|---|---|---|---|---|---|---|---|
| Diet | 1 | 2 | 3 | 4 | 1 | 2 | 3 | 4 |
| Moisture | 119 | 112 | 117 | 118 | 121 | 112 | 115 | 115 |
| Protein | 174 | 181 | 161 | 161 | 164 | 169 | 147 | 147 |
| Fibre | 27 | 26 | 24 | 22 | 28 | 28 | 27 | 26 |
| Fat | 42 | 42 | 42 | 41 | 34 | 34 | 34 | 34 |
| Starch | 418 | 428 | 426 | 429 | 478 | 473 | 475 | 485 |
| Phosphorus | 5.41 | 5.39 | 5.12 | 5.14 | 5.64 | 5.5 | 5.12 | 4.89 |
| Sodium | 3.11 | 3.22 | 3.72 | 3.5 | 2.58 | 2.84 | 3.05 | 2.94 |

Pectin Sources

Pectins with a DE 33 and 55 were isolated from citrus and obtained from Herbstreith & Fox (Neuenburg/Württingen, Germany). The Soy Bean Meal (SBM) was from South-American origin (mixture from Argentina, Brasil and/or Paraguay) and processed to extract the residing pectins by mixing the SBM at 33% dry matter with tapwater and autoclaving for 30 mins at 120 C. After cooling the obtained material was freeze dried and milled, and used as such in the diet.
Experimental Design The experimental design was a complete randomized block design with four treatments.

At weaning, both male and female piglets were assigned to one of the experimental treatments based on body weight, sex and ancestry. Boars and gilts were evenly distributed over treatments, based on the availability of the piglets.

Two periods were distinguished. This was the so-called weaner period (day 0 to 9) and the nursery period (9 to 35 days).

Piglet body weight was measured individually at day before weaning (D-1), D9 and D35. Feed intake was monitored over three periods (D0-D9, D9-35, D0-D35) continuously for the piglets housed in pens equipped with the feeding stations.
Experimental Design

| | | Diet | | | |
|---|---|---|---|---|---|
| | Period | 1 Control | 2 Soy Bean Pectin | 43 DE33 | 4 DE55 |
| Number of meals (per day) | D 0-D 9 | 8.9 | 10.0 | 11.7 | 11.4 |
| | D 9-D 35 | 13.8 | 16.1 | 18.2 | 15.8 |
| Average meal size (g) | D 0-D 9 | 18 | 19 | 19 | 19 |
| | D 9-D 35 | 43 | 41 | 34 | 34 |
| Average meal duration (min) | D 0-D 9 | 4.7 | 4.4 | 4.4 | 3.7 |
| | D 9-D 35 | 6.0 | 6.7 | 4.7 | 5.2 |
| Average eating speed (g/min) | D 0-D 9 | 4.2 | 5.2 | 4.8 | 6.0 |
| | D 9-D 35 | 7.8 | 8.2 | 7.5 | 6.8 |

Surprisingly, pectin fed animals consumed significantly more meals which are in the majority phase of the tests also smaller in size.

Example 6 Incorporation of LM Pectin in Diets Leads to a Healthy Microbiota Composition Piglet Feeding Trial Set-Up The experimental farm for young piglets is located in Flanders (Belgium) and consists of 8 batteries, each containing 4 pens. The piglets under study are hybrids of Topigs Piétrains and are weaned at 21 days. The piglets are weighed individually at weaning and 2 and 4 weeks after weaning. Feed intake is registered per pen of 4 piglets at the moments of weighing. At arrival the piglets are earmarked with a new Sanitel-number. During the trial, a veterinarian and a Felasa D certified person supervise the performed piglet experiment according to the international guidelines described in law EC/86/609.

Each pen (1.5 m×1.5 m) contains 4 piglets at the start of the trial. For each pen, one feeder (ad libitum) is installed for meal or pellets. One drinking nipple is installed per pen. The temperature at start is at 28±2° C. until 10 days after weaning. Afterwards, temperature is decreased to 25±2° C.

Commercial non-medicated diets are given. Non-medicated means that the piglet doesn't receive any therapeutic antibiotics before and during the trial. The diets are given in the form of meal. All feed were analysed for their nutritional content.

Four treatments were applied (diets A, B, C, D) on 7 replicates with 4 piglets per group. At the start of the trial, the piglets (around 7 kg body weight) are allocated to the different pens by weight. This allocation is made in order to have an equal average weight and an equal standard deviation around the average weight for each treatment and pen.

For microbiological counting's and for taking biopsis, piglets receive an overdose of barbiturates (Nembutal) followed by sacrification. Afterwards, a section is performed on the piglets. Samples for microbial counts are immediately processed, while samples taken for histochemical experiments were fixed for later analysis. During the whole trial period the piglets are fed ad libitum, except for the period of microbiological countings. At that moment, three days before the microbiological countings are performed, the piglets are fed restricted. Piglets receive three times a day an amount of feed, which is carefully weighed and noted. The feed is given at 8.00, 13.00 and 18.00. When necessary, the sick piglets were treated individually (by injection). The following parameters were taken into account. (i) individual growth data, (ii) feed intake data per pen (corrected for eventual losses), (iii) feed conversion ratio during weaning, starter and whole trial period, (iv) fecal score and clinical score, (v) tight Junctions, (vi) microbial analysis, (vii) histochemical analysis.

Diets
Feed Compositions (in g/kg):

| Ingredient | Feed A | Feed B | Feed C | Feed D |
|---|---|---|---|---|
| Corn | 171.13 | 169.13 | 169.13 | 169.13 |
| Grains (wheat and barley) | 491.83 | 491.83 | 491.83 | 491.83 |
| Protein sources (soy, potato) | 227.72 | 227.72 | 227.72 | 227.72 |
| Milk derivatives (whey) | 52.65 | 52.65 | 52.65 | 52.65 |
| Soy bean oil | 14.19 | 14.19 | 14.19 | 14.19 |
| Amino acids | 10.80 | 10.80 | 10.80 | 10.80 |
| Minerals & trace minerals | 10.24 | 10.24 | 10.24 | 10.24 |
| Limestone | 10.63 | 10.63 | 10.63 | 10.63 |
| Enzyme* | 0.64 | 0.64 | 0.64 | 0.64 |
| Premix** | 10.17 | 10.17 | 10.17 | 10.17 |
| Pectin DE33 | — | 2.00 | — | — |
| Pectin DE55 | — | — | 2.00 | — |
| Pectin soybean meal | — | — | — | 2.00 |

*Xylanase/beta-glucanase and phytase cocktail (BASF)
** Premix includes aroma's, extra trace minerals, vitamins (Vitamex N.V.)

Pectin Sources

Pectins with a DE 33 and 55 were isolated from citrus and obtained from Herbstreith & Fox (Neuenburg/Württingen, Germany). The Soy Bean Meal (SBM) was from South-American origin (mixture from Argentina, Brasil and/or Paraguay) and processed to liberate the residing pectin. Pectins were extracted from SBM by mixing the SBM at 33% dry matter with tapwater and autoclaving for 30 mins at 120 C. After cooling the obtained material was freeze dried and milled, and used as such in the diet.

Digesta Collection

The pig fecal samples were collected on day 14 and 28 during the experimental diet feeding. After the fecal collection period, animals were anesthetized and euthanized. Digesta samples were collected from terminal ileum, proximal colon, mid colon and distal colon. Part of each digesta was stored in 1.5 mL Eppendorf tubes for analysis of microbiota composition and SCFA. These tubes were immediately frozen in liquid nitrogen and stored at −80° C. The remaining amount of digesta was immediately stored at −20° C. until further analysis.

DNA Extraction and Microbiota Analysis

Microbial DNA was extracted from 250 mg of digesta by using a fecal DNA extraction protocol (Salonen A, Nikkilä J, Jalanka-Tuovinen J, Immonen O, Rajilić-Stojanović M, Kekkonen R A, Palva A & de Vos W M. 2010. Comparative analysis of fecal DNA extraction methods with phylogenetic microarray: Effective recovery of bacterial and archaeal DNA using mechanical cell lysis. Journal of Microbiological Methods, 81: 127-134). The DNA is isolated by sequential precipitations and finally purified by using the QIAamp DNA Stool Mini Kit columns (Qiagen, Hilden, Germany) according to the manufacturer's recommendations. 16S rRNA gene was amplified and sequenced in paired-end mode by using the MiSeq platform (Illumina).

Sequence Analysis

Raw Illumina fastq files were de-multiplexed, quality-filtered and analysed using QIIME 1.9.0.

Relative abundance of Bacteroidetes and Firmicutes species in the microbiota composition of experimental fed pigs

| | | | Relative abundance* | | Ratio** |
|---|---|---|---|---|---|
| Diet | Pectin | Fecal sample | Bacteroidetes | Firmicutes | Bacteroidetes:firmicutes |
| A | control | Terminal ileum | 0 | 0.99 | 0 |
| A | control | Proximal colon | 0.07 | 0.93 | 0.07 |
| A | control | Mid colon | 0.12 | 0.88 | 0.14 |
| A | control | Distal colon | 0.10 | 0.89 | 0.11 |
| B | DE 33 | Terminal ileum | 0 | 1.00 | 0 |
| B | DE 33 | Proximal colon | 0.56 | 0.44 | 1.26 |
| B | DE 33 | Mid colon | 0.63 | 0.36 | 1.75 |
| B | DE 33 | Distal colon | 0.59 | 0.40 | 1.47 |
| C | DE 55 | Terminal ileum | 0 | 0.97 | 0 |
| C | DE 55 | Proximal colon | 0.56 | 0.44 | 1.25 |
| C | DE 55 | Mid colon | 0.48 | 0.51 | 0.94 |
| C | DE 55 | Distal colon | 0.52 | 0.48 | 1.07 |
| D | Soy Bean | Terminal ileum | 0.01 | 0.96 | 0.01 |
| D | Soy Bean | Proximal colon | 0.21 | 0.76 | 0.28 |
| D | Soy Bean | Mid colon | 0.23 | 0.75 | 0.31 |
| D | Soy Bean | Distal colon | 0.31 | 0.66 | 0.47 |

*The relative abundance is the % of 16S rRNA data of Bacteroidetes phylum (the summation of species from the families Porphyromonadaceae, Prevotellaceae, Rikenellaceae as well as species indicated by the codes RF16 and S24-7) and Firmicutes phylum (the summation of species from the families Aerococcaceae, Lactobacillaceae, Streptococcaceae, Christensenellaceae, Clostridiaceae, Lachnospiraceae, Peptostreptococcaceae, Ruminococcaceae, Veillonellaceae, Erysipelotrichaceae) in the total data set obtained through Illumina sequencing
**The ratio is the relative abundance of Bacteroidetes divided by the relative abundance of Firmicutes.

Surprisingly, addition of pectin to the diets leads to an increased ratio of species belonging to the phylum of the Bacteroidetes over species belonging to the phylum of Firmicutes, in the gut. Such a ratio is associated with a reduced prevalence of obesity, and will facilitate managing the body mass index and/or the body fat percentage.

Example 7 Incorporation of LM Pectin in Diets Leads to a Healthy Microbiota Composition The data was acquired and analysed as described in example 6.

| Diet | Pectin | Fecal sample | Prevotellaceae relative abundance* | Prevotellaceae fold increase** | Ruminococcaceae relative abundance* | Ruminococcaceae fold increase** | Lactobacillaceae relative abundance* | Lactobacillaceae fold increase** |
|---|---|---|---|---|---|---|---|---|
| A | control | Terminal ileum | 0 | — | 0.01 | 1 | 0.82 | 1 |
| A | control | Proximal colon | 0.06 | 1 | 0.06 | 1 | 0.71 | 1 |
| A | control | Mid colon | 0.12 | 1 | 0.08 | 1 | 0.64 | 1 |
| A | control | Distal colon | 0.10 | 1 | 0.09 | 1 | 0.57 | 1 |
| B | DE 33 | Terminal ileum | 0 | — | 0.01 | 0.95 | 0.78 | 0.95 |
| B | DE 33 | Proximal colon | 0.55 | 8.55 | 0.05 | 0.95 | 0.46 | 0.66 |
| B | DE 33 | Mid colon | 0.62 | 5.35 | 0.12 | 1.51 | 0.20 | 0.30 |
| B | DE 33 | Distal colon | 0.58 | 5.96 | 0.12 | 1.35 | 0.14 | 0.25 |
| C | DE 55 | Terminal ileum | 0 | — | 0 | — | 0.93 | 1.19 |
| C | DE 55 | Proximal colon | 0.54 | 8.40 | 0.15 | 2.59 | 0.03 | 0.05 |
| C | DE 55 | Mid colon | 0.47 | 4.06 | 0.16 | 2.05 | 0.01 | 0.02 |
| C | DE 55 | Distal colon | 0.50 | 5.15 | 0.15 | 1.70 | 0.01 | 0.02 |
| D | Soy Bean | Terminal ileum | 0 | — | 0 | — | 0.52 | 0.66 |
| D | Soy Bean | Proximal colon | 0.21 | 3.30 | 0.18 | 3.09 | 0.03 | 0.05 |
| D | Soy Bean | Mid colon | 0.23 | 1.97 | 0.15 | 1.94 | 0.03 | 0.04 |
| D | Soy Bean | Distal colon | 0.31 | 3.16 | 0.20 | 2.30 | 0.01 | 0.02 |

*The relative abundance is the % of 16S rRNA data of families of Prevotellaceae (the summation of species from the genus *Prevotella*), Ruminococcaceae (the summation of species from the genus *Ruminococcus*) and Lactobacillaceae (the summation of species from the genus *Lactobacillus*) in the total data set obtained through Illumina sequencing
**The fold increase is the relative increase in % of specific 16S rRNA in the total data set, i.e. the relative abundance of determined for a specific pectin fed sample divided by the correspondingcontrol sample.

Surprisingly, addition of pectin to the diets leads to an relative increase in presence of species belonging to the families of the Prevotellaceae and Ruminococcaceae, as well as a relative decrease in presence of species belonging family of Lactobacillaceae, in the gut. Such shifts in microbiota are associated with a reduced prevalence of obesity, and will facilitate managing the body mass index and/or the body fat percentage.

All these examples clearly and surprisingly show that the specific pectins show improvements, which are of significant importance in managing the body mass index, the body fat percentage and/or the distribution of fat storage sites.

The invention claimed is:

1. A method of managing visceral fat of a human, the method comprising administering to the human in need of managing visceral fat a food formulation comprised of a low methylated (LM) pectin having a degree of esterification (DE) of at least 1% to less than 50% to achieve an effective amount of the LM pectin of 0.01 g to 5 g per Kg of body weight of the human per day.

2. The method according to claim 1, wherein the LM pectin is not amidated.

3. The method according to claim 1, wherein the method further comprises obtaining the LM pectin by the steps comprising:
   (i) extracting a high methylated (HM) pectin having a DE of more than 50% from a pectin containing plant;
   (ii) controlling acidity, temperature and time of extraction according to step (i) to obtain the LM pectin; and
   (iii) including the LM pectin in the food formulation administered to the human in need of managing visceral fat.

* * * * *